(12) United States Patent
Choi et al.

(10) Patent No.: US 10,687,768 B2
(45) Date of Patent: Jun. 23, 2020

(54) X-RAY IMAGE FORMING DEVICE

(71) Applicants: VATECH Co., Ltd., Gyeonggi-do (KR); VATECH EWOO Holdings Co., Ltd., Gyeonggi-do (KR)

(72) Inventors: Sung Il Choi, Gyeonggi-do (KR); Woong Bae, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 378 days.

(21) Appl. No.: 15/512,538

(22) PCT Filed: Sep. 18, 2015

(86) PCT No.: PCT/KR2015/009848
§ 371 (c)(1),
(2) Date: Mar. 17, 2017

(87) PCT Pub. No.: WO2016/043562
PCT Pub. Date: Mar. 24, 2016

(65) Prior Publication Data
US 2017/0281101 A1    Oct. 5, 2017

(30) Foreign Application Priority Data
Sep. 18, 2014  (KR) .................. 10-2014-0124528

(51) Int. Cl.
| | |
|---|---|
| A61B 6/14 | (2006.01) |
| A61B 6/00 | (2006.01) |
| G06T 3/40 | (2006.01) |
| H05G 1/02 | (2006.01) |
| H05G 1/60 | (2006.01) |
| A61B 6/03 | (2006.01) |

(52) U.S. Cl.
CPC .............. *A61B 6/14* (2013.01); *A61B 6/4435* (2013.01); *A61B 6/461* (2013.01); *A61B 6/5211* (2013.01);
(Continued)

(58) Field of Classification Search
CPC .......... A61B 6/032; A61B 6/14; A61B 6/405; A61B 6/4435; A61B 6/461; A61B 6/5205;
(Continued)

(56) References Cited

U.S. PATENT DOCUMENTS 5,093,852 A    3/1992  Nishikawa et al.
6,493,415 B1   12/2002  Arai et al.
(Continued)

FOREIGN PATENT DOCUMENTS

CN    102469977 A    5/2012
CN    103096804 A    5/2013
(Continued)

OTHER PUBLICATIONS

European Patent Office, Extended European Search Report of corresponding EP Patent Application No. 15842725.2, dated May 29, 2018.

*Primary Examiner* — Irakli Kiknadze
(74) *Attorney, Agent, or Firm* — IP Legal Services, LLC

(57) ABSTRACT

Disclosed is an X-ray image forming device is disclosed. The device includes an X-ray imaging unit including a rotating member rotatable about a rotating shaft and linearly movable, and an X-ray source and an X-ray sensor disposed at opposite ends of the rotating member to face each other with a region of interest therebetween, a penetration data acquisition unit configured to acquire X-ray penetration data from multiple directions crossing through an image layer in the region of interest by controlling the X-ray imaging unit and an image reconstructor configured to generate projection data in a predetermined angle range at each section of the image layer from the X-ray penetration data, and reconstruct a two-dimensional X-ray panoramic image of the image layer based on the projection data.

12 Claims, 9 Drawing Sheets

(52) U.S. Cl.
CPC ............. *G06T 3/4038* (2013.01); *H05G 1/02* (2013.01); *H05G 1/60* (2013.01); *A61B 6/032* (2013.01); *A61B 6/405* (2013.01); *A61B 6/5205* (2013.01)

(58) Field of Classification Search
CPC ....... A61B 6/5211; A61B 6/145; A61B 6/025; A61B 6/037; A61B 6/4405; A61B 6/4429; A61B 6/466; A61B 6/469; A61B 6/4021; A61B 6/4233; A61B 6/4241; A61B 6/501; A61B 6/5258; A61B 6/027; A61B 6/035; A61B 6/4028; A61B 6/463; A61B 6/5223; A61B 6/5241; A61B 6/542; A61B 6/544; A61B 6/547; A61B 6/4441; A61B 6/4452; A61B 17/12022; A61B 17/12118; A61B 17/12131; A61B 2017/1205; A61B 6/0478; A61B 6/06; G06T 3/4038; G06T 2207/10116; G06T 2207/30036; G06T 7/55; G06T 7/579; G06T 7/97; H05G 1/02; H05G 1/60; H05G 1/36; H05G 1/44; G01N 2223/419; G01N 23/046; G01T 1/1642; G01T 1/247; G03B 42/042; B01J 21/16; B01J 29/049; H04L 2209/122; H04L 2209/125; H04L 2209/24; H04L 9/0625
USPC .............................................. 378/4, 9, 19, 38
See application file for complete search history.

(56) References Cited

U.S. PATENT DOCUMENTS

| | | | |
|---|---|---|---|
| 7,336,763 B2 | 2/2008 | Spartiotis et al. | |
| 7,676,022 B2 * | 3/2010 | Pantsar | A61B 6/14 378/38 |
| 8,244,017 B2 * | 8/2012 | Chun | G06T 7/50 382/131 |
| 8,320,522 B2 | 11/2012 | Ulrici et al. | |
| 9,036,776 B2 * | 5/2015 | Sadakane | A61B 6/145 378/38 |
| 9,538,966 B2 * | 1/2017 | Muller | A61B 6/5229 |
| 9,668,705 B2 * | 6/2017 | Yamakawa | A61B 6/14 |
| 2004/0066877 A1 | 4/2004 | Arai et al. | |
| 2006/0203959 A1 | 9/2006 | Spartiotis et al. | |
| 2008/0019477 A1 | 1/2008 | Spartiotis et al. | |
| 2008/0063139 A1 | 3/2008 | Pantsar et al. | |
| 2009/0232274 A1 | 9/2009 | Spartiotis et al. | |
| 2009/0232275 A1 | 9/2009 | Spartiotis et al. | |
| 2010/0034340 A1 | 2/2010 | Spartiotis et al. | |
| 2010/0054403 A1 | 3/2010 | Ro et al. | |
| 2010/0142673 A1 | 6/2010 | Pantsar et al. | |
| 2010/0208866 A1 | 8/2010 | Spartiotis et al. | |
| 2010/0246761 A1 | 9/2010 | Pantsar et al. | |
| 2012/0230467 A1 * | 9/2012 | Katsumata | A61B 6/032 378/19 |
| 2013/0003921 A1 | 1/2013 | Spartiotis et al. | |
| 2013/0329854 A1 | 12/2013 | Spartiotis et al. | |
| 2015/0146853 A1 | 5/2015 | Spartiotis et al. | |
| 2015/0305696 A1 | 10/2015 | Yamakawa et al. | |
| 2016/0015332 A1 | 1/2016 | Katsumata et al. | |

FOREIGN PATENT DOCUMENTS

| | | |
|---|---|---|
| EP | 2614773 A1 | 7/2013 |
| JP | 4015366 B2 | 11/2007 |
| JP | 2010-011910 A | 1/2010 |
| KR | 10-0861409 B1 | 10/2008 |
| KR | 10-2010-0070817 A | 6/2010 |
| KR | 10-2010-0121653 A | 11/2010 |
| KR | 10-1244136 B1 | 3/2013 |
| KR | 10-2014-0008287 A | 1/2014 |

* cited by examiner (a)

(b)

X-RAY IMAGE FORMING DEVICE

CROSS REFERENCE TO RELATED APPLICATIONS

This application is a National Stage Patent Application of PCT International Patent Application No. PCT/KR2015/009848 (filed on Sep. 18, 2015) under 35 U.S.C. § 371, which claims priority to Korean Patent Application No. 10-2014-0124528 (filed on Sep. 18, 2014), the teachings of which are incorporated herein in their entireties by reference.

TECHNICAL FIELD

The present invention relates generally to digital X-ray image processing. More particularly, the present invention relates to an X-ray panoramic image forming device and an X-ray panoramic image forming method based on X-ray penetration data from multiple directions of a subject.

BACKGROUND ART

X-ray radiography is a radiography method using straightness and attenuation of X-rays, and based on the amount of attenuation accumulated in the course of the X-rays passing through an FOV (field of view), it is used to obtain a visual image of the internal structure of the FOV. In recent years, X-ray radiography has been rapidly evolving into Digital Radiography (DR) using digital sensors due to the development of semiconductor and information processing technologies, whereby image processing technology has also been developed and used in various ways according to the purpose and application field.

Among X-ray radiography, dental panoramic X-ray radiography is widely known in the dental field, wherein an X-ray panoramic image by this imaging method is an image for showing the entire dentition part of the human head. In particular, the X-ray panoramic image is advantageous in that a tooth and tissue therearound based on any image layer in the dental arch, or a two-dimensional transmission image of an arrangement relation between the jawbone and cervical vertebrae can be seen. The X-ray panoramic image is used as a standard image most familiar to dentists because it can be used to easily identify the overall arrangement of a tooth and tissue therearound with only a single image.

According to typical X-ray radiography, X-ray penetration data for each section of the image layer is formed while shifting the focal distance between the X-ray sensor and the X-ray source along the curved image layer corresponding to the dental arch trajectory, and X-ray penetration data is appropriately superimposed on a two-dimensional plane to form an X-ray panoramic image for the image layer. To achieve this, the rotating shaft between the X-ray sensor and the X-ray source is driven by a two-axis drive system that performs rotational and linear motion. This type of X-ray radiography is commonly referred to as a 'shift-and-add (SAA) method' or a 'panoramic scanning technique'.

The X-ray beam from the X-ray source has a predetermined width and height. The width of the X-ray sensor for imaging an X-ray panoramic image is limited to below a predetermined range so that the curve shape of the image layer can be reflected in the X-ray penetration data for each section. The X-ray sensor for imaging an X-ray panoramic image is slit shaped with a width of about 5~20 mm, and when the width is out of the width range, a so-called blur phenomenon appears, in which the entire X-ray panoramic image is blurred. However, when the X-ray panoramic image is radiographed using the X-ray sensor with such a small width, the cervical vertebrae is included in the image along with the dental arch. The cervical vertebrae is not the subject of dental diagnosis or treatment, and when a dental X-ray panoramic image contains the cervical vertebrae, the cervical vertebrae overlaps the tooth area to reduce the sharpness of the tooth structure image, and ghost effects or artifacts may be increased.

The X-ray source and the X-ray sensor are provided at opposite ends of a moving member having a predetermined length, wherein a rotating shaft of the moving member is rotated or linearly moved by the two-axis drive system as described above. In the panoramic scanning technique, the rotating shaft should perform a fast linear motion at the start and end of imaging, and during imaging of molar teeth, but perform a slow linear motion during imaging of frontal teeth. Accordingly, a speed of the linear motion of the rotating shaft should be appropriately changed, so it is necessary to control the heavy moving member to be linearly moved while being accurately accelerated and decelerated. As a result, the mechanical structure of the X-ray panoramic imaging apparatus becomes complicated, and in particular, there arises a problem that an excessive load may be applied to the machine during the acceleration and deceleration in the linear motion.

To minimize or prevent the inclusion of images of the cervical vertebrae in the X-ray panoramic image, a panoramic image obtaining apparatus of a three-axis drive system, which performs panoramic imaging without generating X-rays transmitted through a cervical vertebrae by using a three-axis moving member, has been proposed (see Korean Patent No. 10-0861409). However, the proposed apparatus is problematic in that it is required to accelerate and decelerate the moving member in two directions, which is a heavy and large mechanical structure, and thus has a large mechanical burden.

A computed tomography (CT; hereinbelow, referred to as "CT") is known as a method for acquiring an X-ray panoramic image without using panoramic X-ray radiography. A general X-ray CT image displays a three-dimensional X-ray CT image of the entire FOV based on a computed tomographic image throughout the entire area of the FOV. Since the X-ray CT image is able to accurately and clearly display a tomographic image according to user's desired location and direction, as well as a three-dimensional X-ray CT image of FOV, it is mainly used in fields requiring high precision, such as implant procedure in dentistry. As described above, when an image layer is assigned to a previously acquired X-ray CT image and a tomographic image thereof is reconstructed, an X-ray panoramic image for the corresponding image layer can be obtained. The method of acquiring the X-ray panoramic image is generally referred to as a panoramic reconstruction method using a three-dimensional X-ray CT image'.

The panoramic reconstruction method is relatively advantageous in that it is performed such that three-dimensional X-ray CT image of FOV is obtained in advance by one X-ray CT imaging apparatus, and based on the three-dimensional X-ray CT image, an X-ray panoramic image is obtained. However, the panoramic reconstruction method is problematic in that a large amount of arithmetic units and much time is required to process arithmetic because the amount of computation required for reconstructing a panoramic image is too large. The panoramic reconstruction method is further problematic in that radiography with high a dose of X-rays needs to be performed unnecessarily in order to obtain an X-ray panoramic image. The panoramic reconstruction method is further problematic in that it may be somewhat heterogeneous to users who are familiar with the panoramic scanning technique because of their different quality from that of the panoramic scanning technique. Therefore, there is still a need for a new X-ray panoramic image forming apparatus capable of reducing the data processing burden and the mechanical burden while maintaining image quality.

DISCLOSURE

Technical Problem

Accordingly, the present invention has been made keeping in mind the above problems occurring in the prior art, and an object of the present invention is to provide a new X-ray image forming device and an X-ray image forming method capable of forming an X-ray panoramic image in a manner different from a conventional panoramic scanning technique or a panoramic reconstruction method.

Another object of the present invention is to provide an X-ray image forming device and an X-ray image forming method, in which there is no limit to a width of an X-ray sensor and a driving method of an imaging equipment required in the conventional panoramic scanning technique and unlike conventional panoramic reconstruction method, a reliable X-ray panoramic image can be formed by minimum calculation.

The objectives presented by the present invention are not limited to the objectives mentioned above, and other objectives not mentioned may be clearly understood by those skilled in the art from the following description.

Technical Solution

In order to accomplish the above object, the present invention provides an X-ray image forming device. The device includes: an X-ray imaging unit including a rotating member which is rotatable about a rotating shaft and linearly movable, and an X-ray source and an X-ray sensor disposed at opposite ends of the rotating member to face each other with a region of interest therebetween; a penetration data acquisition unit configured to acquire X-ray penetration data from multiple directions crossing through an image layer in the region of interest by controlling the X-ray imaging unit; and an image reconstructor configured to generate projection data in a predetermined angle range at each section of the image layer from the X-ray penetration data, and reconstruct a two-dimensional X-ray panoramic image of the image layer based on the projection data.

In an embodiment, the image reconstructor may reconstruct the two-dimensional X-ray panoramic image by back-projecting the projection data at each section of the image layer.

In an embodiment, the predetermined angle range may be 10 degrees or more and less than 180 degrees including a normal direction at each section of the image layer.

In an embodiment, the region of interest may include a dental arch, the image layer may be within the dental arch, and the predetermined angle range may gradually increase from a molar tooth to an anterior tooth.

In an embodiment, the image reconstructor may include an interpolation data generator configured to generate interpolation data in the predetermined angle range at each section of the image layer from the X-ray penetration data and generate the projection data based on both the X-ray penetration data and the interpolation data.

In an embodiment, the device may further include a projection data compensator configured to constantly compensate a number and a distance of the projection data at each section of the image layer.

In an embodiment, the rotating shaft may move linearly at a constant velocity to acquire the X-ray penetration data.

In an embodiment, the X-ray sensor may have a width of 6 mm or more and 100 mm or less.

In an embodiment, the X-ray sensor may have a width of 20 mm or more and 70 mm or less.

In an embodiment, the region of interest may include a dental arch, and the rotating member may move linearly along a centerline passing through a center of an anterior tooth of the dental arch at a distance of 0 to 60 mm, to acquire the X-ray penetration data.

In an embodiment, the rotating member may move linearly along the centerline passing through the center of the anterior tooth of the dental arch at a distance of 20 mm to 50 mm, to acquire the X-ray penetration data.

In an embodiment, the rotating member may include at least one condition of three conditions: a first condition that the rotating shaft moves linearly at a constant velocity to acquire the X-ray penetration data; a second condition that the X-ray sensor has a width of 20 mm or more and 50 mm or less; and a third condition that the rotating member moves linearly forwards and backwards along a centerline of the dental arch at a distance of 20 mm to 50 mm to acquire the X-ray penetration data.

In an embodiment, the penetration data acquisition unit may control the X-ray imaging unit such that the X-ray penetration data includes penetration data penetrating through a substantial entire area of the region of interest by respectively penetrating through a part of the region of interest, and the image reconstructor may reconstruct a three-dimensional CT image of the entire region of interest based on the X-ray penetration data.

In an embodiment, the device may further include a display configured to selectively or simultaneously display the two-dimensional panoramic image and the three-dimensional CT image on a screen.

According to embodiments of the present invention, there is further provided an X-ray image forming method. The method may be performed by using an X-ray imaging unit including a rotating member rotatable about a rotating shaft and linearly movable, and an X-ray source and an X-ray sensor disposed at opposite ends of the rotating member to face each other with a region of interest therebetween. The X-ray image forming method may include: (a) acquiring X-ray penetration data from multiple directions crossing through an image layer in the region of interest by controlling the X-ray imaging unit; (b) generating projection data in a predetermined angle range at each section of the image layer from the X-ray penetration data; and (c) reconstructing a two-dimensional X-ray panoramic image of the image layer based on the projection data.

In an embodiment, the step (c) may include reconstructing the two-dimensional X-ray panoramic image by backprojecting the projection data at each section of the image layer.

In an embodiment, the predetermined angle range may be 10 degrees or more and less than 180 degrees including a normal direction at each section of the image layer.

In an embodiment, the step (b) may include generating interpolation data in the predetermined angle range at each section of the image layer from the X-ray penetration data and generating the projection data based on both the X-ray penetration data and the interpolation data.

In an embodiment, the step (b) may include constantly compensating a number and a distance of the projection data at each section of the image layer.

In an embodiment, the rotating shaft may move linearly at a constant velocity.

In an embodiment, the X-ray sensor may have a width of 6 mm or more and 100 mm or less.

In an embodiment, the X-ray sensor may have a width of 20 mm or more and 50 mm or less.

In an embodiment, the region of interest may include a dental arch, and the rotating shaft may move linearly along a centerline passing through a center of an anterior tooth of the dental arch at a distance of 0 to 60 mm.

In an embodiment, the rotating shaft may move linearly along the centerline passing through the center of the anterior tooth of the dental arch at a distance of 20 mm to 60 mm.

In an embodiment, the rotating member may include at least one condition of three conditions: a first condition that the rotating shaft moves linearly at a constant velocity to acquire the X-ray penetration data; a second condition that the X-ray sensor has a width of 20 mm or more and 50 mm or less; and a third condition that the rotating member moves linearly forwards and backwards along a centerline of the dental arch at a distance of 20 mm to 50 mm to acquire the X-ray penetration data.

In an embodiment, the step (a) may include acquiring penetration data penetrating through a substantial entire area of the region of interest by respectively penetrating through a part of the region of interest, as the X-ray penetration data; the step (c) may include reconstructing a three-dimensional CT image of the entire region of interest based on the X-ray penetration data; and the method may further include selectively or simultaneously displaying the two-dimensional panoramic image and the three-dimensional CT image on a screen, after the step (c).

Advantageous Effects

According to the X-ray image forming device and the method proposed by the present invention the present invention, it is possible to form a three-dimensional X-ray CT image of a region of interest or a two-dimensional X-ray panoramic image of any image layer in a dental arch through a simple calculation by using X-ray penetration data from multiple directions of the region of interest of a subject including the dental arch.

The present invention is advantageous in that since a three-dimensional X-ray CT image and an X-ray panoramic image of a subject may be formed without any limitations to order through one time of radiography by using a single imaging device with a single drive system and sensor, thereby it is possible to prevent unnecessary economic loss due to separate imaging of an X-ray panoramic image and an X-ray CT image, and is possible to significantly reduce the amount of X-ray exposure applied to the subject.

The present invention is further advantageous in that there is no limit to a width of an X-ray sensor and a driving method of an imaging equipment required in the conventional panoramic scanning technique and unlike conventional panoramic reconstruction method, a reliable X-ray panoramic image can be formed by minimum calculation.

MODE FOR INVENTION

Detailed features and advantages of the present invention will be apparent from the following detailed description based on the accompanying drawings. However, it should be understood that the embodiment of the present invention may be changed to a variety of embodiments and the scope and spirit of the present invention are not limited to the embodiment described hereinbelow. The embodiment of the present invention described hereinbelow is provided for allowing those skilled in the art to more clearly comprehend the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

In the embodiment of the present invention described hereinbelow, the term 'module' or 'unit' means a functional part performing at least one function or action, which may be realized with a hardware or a software, or a combination of a hardware and a software. Further, except 'module' or 'unit' that needs to be realized with a specific hardware, a plurality of 'modules' or a plurality of 'parts' may be integrated into at least one module to be realized as at least one processor.

In addition, unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, preferred embodiments of the present invention will be described in detail with reference to the accompanying drawings. In the following description, it is to be noted that, when the functions of conventional elements and the detailed description of elements related with the present invention may make the gist of the present invention unclear, a detailed description of those elements will be omitted.

Figure 1:
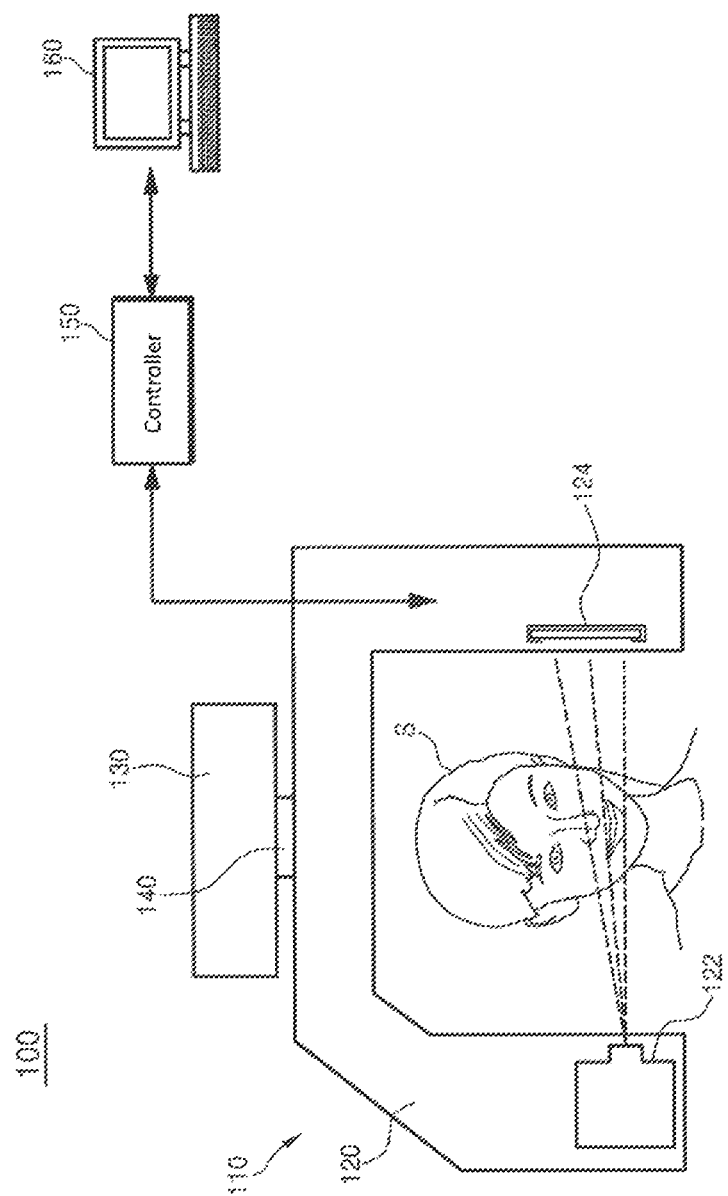
FIG. 1 is a schematic sectional diagram illustrating an entire configuration of an X-ray image forming device according to an embodiment of the present invention.
Figure 2:
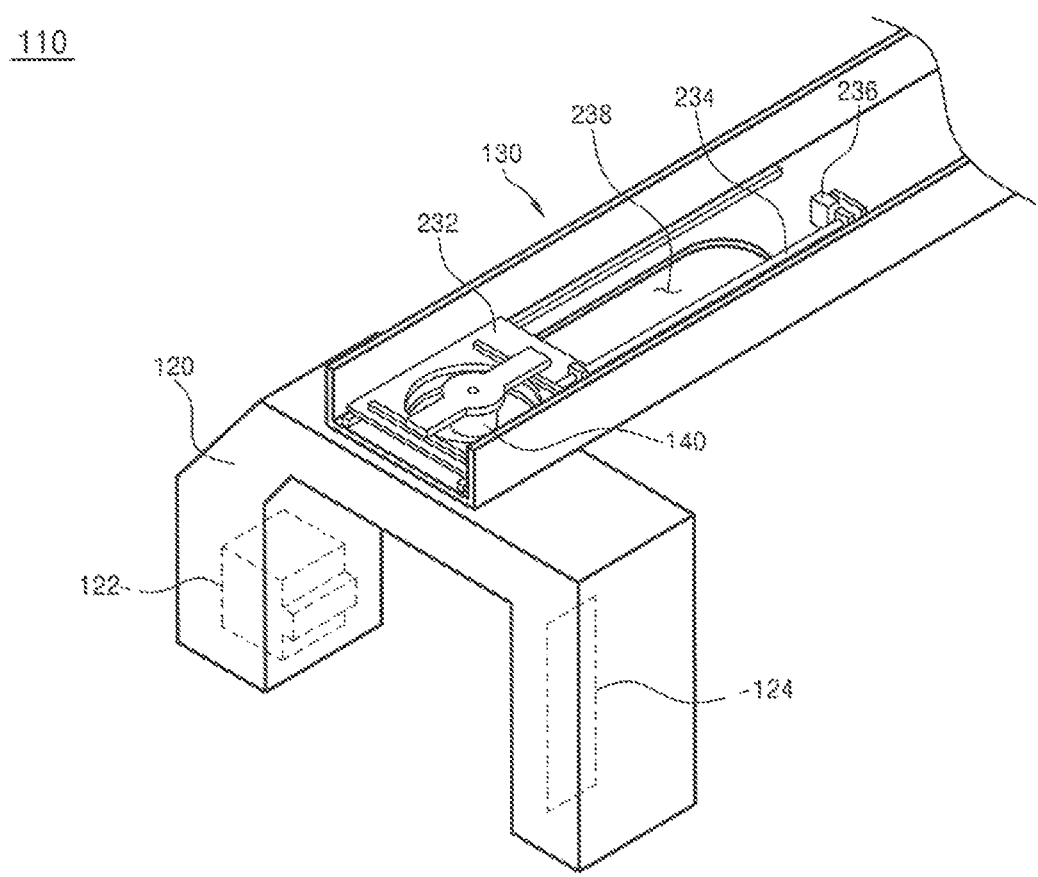
FIG. 2 is a schematic three-dimensional diagram illustrating an embodiment of a partial configuration of an X-ray imaging unit of the X-ray image forming device shown in FIG. 1.

FIG. 1 is a schematic sectional diagram illustrating an entire configuration of an X-ray image forming device according to an embodiment of the present invention; and FIG. 2 is a schematic three-dimensional diagram illustrating an embodiment of a partial configuration of an X-ray imaging unit of the X-ray image forming device shown in FIG. 1.

Referring to FIGS. 1 and 2, an X-ray image forming device 100 may include an X-ray imaging unit 110, a controller 150, and an input/output unit 160.

The X-ray imaging unit 110 may be configured to include: a rotating member 120 having an X-ray source 122 and an X-ray sensor 124 disposed at opposite ends of the rotating member to face each other; a rotating shaft 140 configured to rotate the rotating member 120; and a fixing member 130 configured to allow the rotating member 120 to rotate by the rotating shaft 140 and linearly move the rotating shaft 140. The X-ray source 122 is capable of emitting an X-ray beam toward a subject S, and may include an adjusting means, such as a collimator, configured to adjust an irradiation angle and an irradiation area of the X-ray beam. The X-ray sensor 124 that is disposed to face the X-ray source 122 is capable of detecting an X-ray beam (see a dotted line of FIG. 1) that has penetrated through the subject S by being emitted from the X-ray source 122 toward the subject S.

In an embodiment, the X-ray sensor 124 may be configured as a CCD or a CMOS image sensor array, but its configuration is not limited thereto. According to the embodiment of the present invention, a width of the X-ray sensor 124 needs not to be small, unlike a conventional panoramic scanning technique, and thus it is not limited to a specific size. Assuming that the minimum unit for location distinction of the image layer corresponds to one pixel of the X-ray sensor 124, the width of the X-ray sensor 124 is sufficient to provide an X-ray incident area of one pixel line or more. However, considering imaging efficiency, the width of the X-ray sensor 124 may be determined within the range from a width of an X-ray sensor in the conventional panoramic scanning technique to a width of a CT sensor (magnification ratio×a width of FOV). In an embodiment, the width of the X-ray sensor 124 may be selected within the range from 5 mm to 300 mm, but is not limited thereto.

The rotating member 120 may be configured such that the subject S is placed between the X-ray source 122 and the X-ray sensor 124. In an embodiment, the rotating member 120 may include: a bar extending in a horizontal direction by a predetermined distance; and vertical end portions being in the form of a gantry that is integrally coupled to the bar and extending downward therefrom with the X-ray source 122 and the X-ray sensor 124 mounted thereto being apart from each other at a predetermined distance, but the configuration of the rotating member 120 is not limited thereto. The rotating member 120 is not limited to a specific configuration as long as the rotating member 120 is capable of rotating along an outer circumference of the subject S and allows the subject S to be placed in the X-ray beam path between the X-ray source 122 and the X-ray sensor 124 so that the X-ray source 122 and the X-ray sensor 124 can perform radiography of the subject S in multiple directions.

The rotating shaft 140 may be configured to be coupled to the rotating member 120 or to the fixing member 130, so as to serve as a shaft that transmits a torque from a rotation drive motor (not shown) to the rotating member 120. Through this, the rotating shaft 140 may be designed to perform a mechanical role to allow the rotating member 120 and the fixing member 130 to be coupled thereto.

The fixing member 130 may be supported by a support member (not shown). The fixing member 130 may be configured to fix the rotating shaft 140 rotating the rotating member 120 and linearly drive the rotating shaft 140. In an embodiment, the fixing member 130 may include: a guide plate configured to linearly drive the rotating shaft 140; and a linear drive motor 236 fixed to a housing of the fixing member 130 to linearly drive the guide plate 232. In an embodiment, a lower plate of the housing of the fixing member 130 may be provided with a guide groove 238 to guide the movement of the rotating shaft 140 that is attached to the guide plate 232. According to the above described configuration, the rotating member 120 can perform rotation drive and linear drive simultaneously, thereby moving and rotating along a path suitable for performing radiography of the region of interest of the subject S.

The guide plate 232 may be fixed not to be rotated by side plates of the housing of the fixing member 130. Thereby, when the rotating shaft 140 is rotated, the rotating member 120 coupled to the rotating shaft 140 is capable of rotating about the rotating shaft 140 relative to the fixing member 130.

When the linear drive motor 236 fixed to the housing of the fixing member 130 is operated, a screw 234 that is configured to be connected to a shaft of the linear drive motor 236 at a first end thereof and connected to a nut fixed to the guide plate 232 at a second end thereof is rotated, and the nut reciprocates along the screw 234 in a rotation direction of the screw 234, whereby the rotating shaft 140 can move linearly.

Referring again to FIG. 1, the X-ray imaging unit 110 may be configured to acquire X-ray penetration data of the region of interest from multiple directions by detecting the X-ray penetration data that has penetrated through the subject S by emitting the X-ray beam onto the region of interest of the subject S.

The controller 150 may be configured to acquire the X-ray penetration data of the region of interest from the X-ray sensor 124 by controlling the X-ray imaging unit 110 such that the X-ray beam is emitted from the X-ray source 122 to the region of interest of the subject S to penetrate through the region of interest as the rotating member 120 rotates and is linearly driven. The controller 150 may be configured to form a two-dimensional X-ray panoramic image of an image layer in a trajectory of a dental arch and/or a three-dimensional X-ray CT image of the entire region of interest, by image processing the X-ray penetration data detected by the X-ray sensor 124.

The input/output unit 160 may be configured to allow a user to input data relating to an imaging plan and display the two-dimensional X-ray panoramic image formed according to the present invention including various imaging parameters and/or the three-dimensional X-ray CT image. The input/output unit 160 may include an input means, such as a keyboard, a keypad, and a touchpad, an output means, such as a printer, a display, and a speaker, and a communication module, but does not limited thereto.

Figure 3:
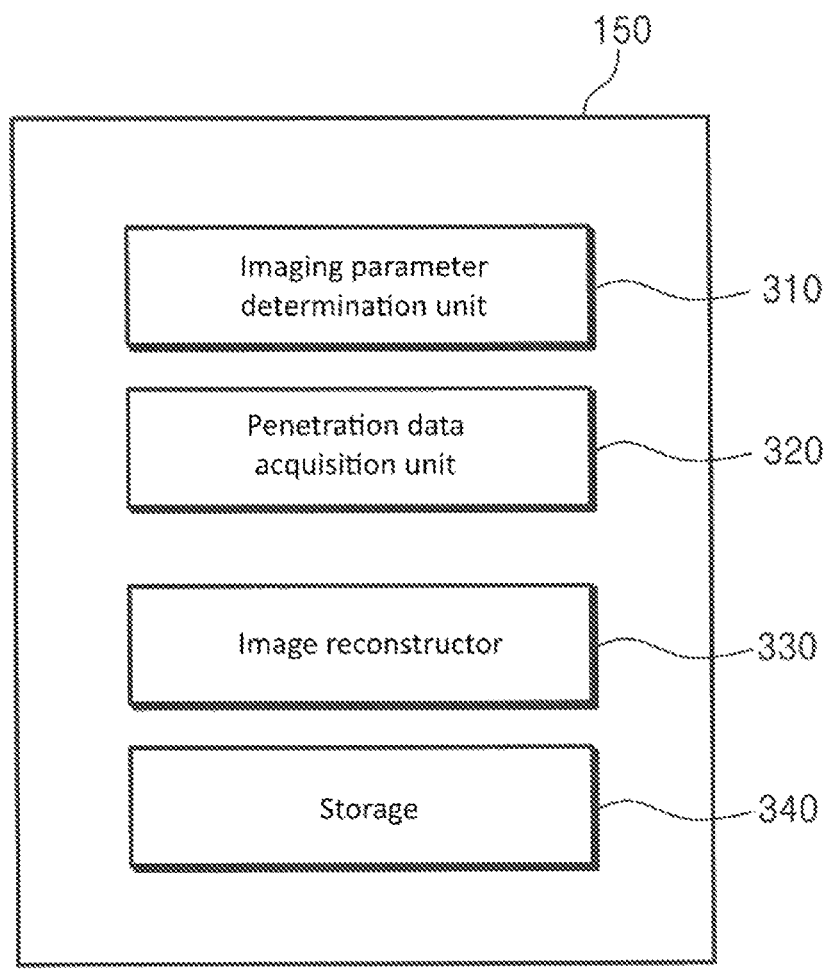
FIG. 3 is a block diagram illustrating an embodiment of a configuration of a controller of the X-ray image forming device shown in FIG. 1.
Figure 4:
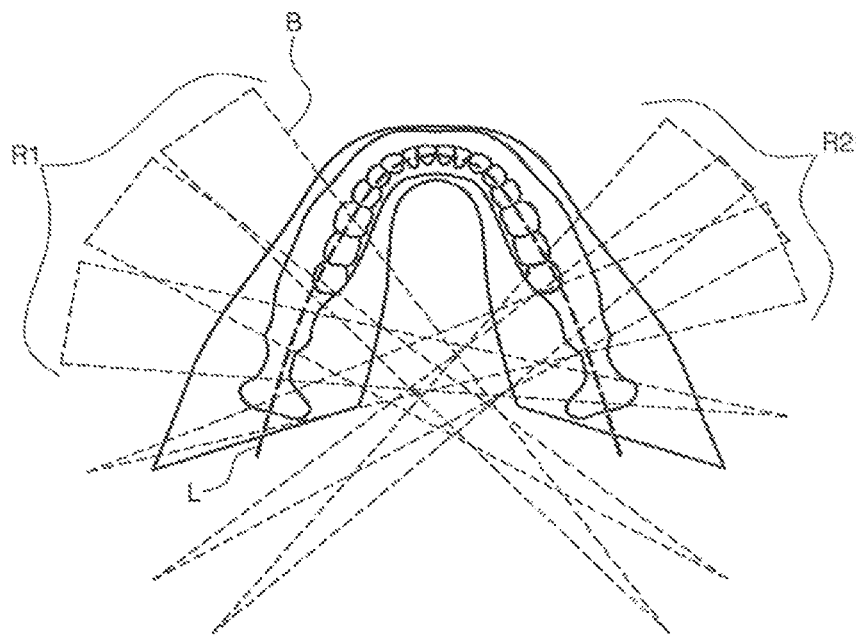
FIG. 4 is a view illustrating an embodiment of how a penetration data acquisition unit controls the X-ray imaging unit according to an imaging density determined by an imaging parameter determination unit.

FIG. 3 is a block diagram illustrating an embodiment of a configuration of a controller of the X-ray image forming device shown in FIG. 1; and FIG. 4 is a view illustrating an embodiment of how a penetration data acquisition unit controls the X-ray imaging unit according to an imaging density determined by an imaging parameter determination unit.

Referring to FIG. 3, the controller 150 may include an imaging parameter determination unit 310, a penetration data acquisition unit 320, an image reconstructor 330, and a storage 340.

The imaging parameter determination unit 310 may be configured to determine imaging parameters relating to radiography. According to an embodiment, the imaging parameters may include a region of interest of a subject, an image layer in the region of interest, an imaging trajectory, an imaging density according to the imaging trajectory, and the like. Herein, the term 'imaging trajectory' may refer to a trajectory that is set throughout a region of interest, in which a predetermined width of the X-ray beam scanning the region of interest moves. In other words, the term 'imaging trajectory' may correspond to a trajectory, in which the X-ray source 122 and the X-ray sensor 124 move. According to an embodiment, the imaging parameter determination unit 310 may be configured to allow the user to select some or all of the imaging parameters through the input means, such as a keyboard, a keypad, and a touchpad. For example, the imaging parameter determination unit 310 may be configured such that the user selects a specific image layer, the imaging trajectory is divided into more than two sections, and a different imaging density from each other is selected for each section. According to an embodiment, the imaging parameter determination unit 310 may be configured to select imaging parameters that are stored therein in advance.

To be more specific to the imaging density, the imaging density may be expressed as a ratio of irradiation times of X-ray beam to a length of the imaging trajectory, namely, as the following Equation 1.

$$\text{imaging density} = \text{number of irradiation times of X-ray beam}/\text{length of imaging trajectory} \quad \text{Equation 1:}$$

According to Equation 1, when a value of the imaging density is larger, the number of times the X-ray beam of the X-ray source 122 is irradiated while the rotating member 120 of the X-ray imaging unit 110 rotates along a predetermined length of the imaging trajectory; on the contrary, when a value of the imaging density is smaller, the number of times the X-ray beam of the X-ray source 122 is irradiated while the rotating member 120 of the X-ray imaging unit 110 rotates along a predetermined length of the imaging trajectory. In an embodiment, the imaging density may be configured to have one value throughout the entire length of the imaging trajectory. On the contrary, the length of the imaging trajectory may be divided into multiple sections, and the imaging density may have a different value from section to section.

The penetration data acquisition unit 320 may be operated in a state where the subject S is placed between the X-ray source 122 and the X-ray sensor 124 of the X-ray imaging unit 110 in order to acquire the X-ray penetration data of the region of interest of the subject S. The penetration data acquisition unit 320 may be configured to control the X-ray imaging unit 110 in order to acquire the X-ray penetration data of the region of interest of the subject S. In other words, the penetration data acquisition unit 320 may be configured to control the X-ray imaging unit 110 such that the rotating member 120 of the X-ray imaging unit 110 rotates about the rotating shaft 140, and the rotating shaft 140 of the rotating member 120 is linearly driven, whereby the X-ray beam is emitted from the X-ray source 122 to the region of interest of the subject S to penetrate through the region of interest.

The penetration data acquisition unit 320 may be configured to control the X-ray imaging unit 110 according to at least one parameter relating to radiography that is determined by the imaging parameter determination unit 310. For example, the penetration data acquisition unit 320 may be configured to control the X-ray imaging unit 110 such that the rotating member 120 of the X-ray imaging unit 110 rotates and moves along the imaging trajectory determined by the imaging parameter determination unit 310. In an embodiment, the penetration data acquisition unit 320 may be configured to control the X-ray imaging unit 110 such that the X-ray beam is emitted to a part of the region of interest that corresponds to an imaging trajectory as many as the number of times determined according to the imaging density that is determined at each section of the imaging trajectory by the imaging parameter determination unit 310. Referring to FIG. 4, which is a view illustrating an embodiment of how a penetration data acquisition unit controls the X-ray imaging unit according to an imaging density determined by an imaging parameter determination unit, it is conceptually shown that the X-ray beam B scans a dental arch of the subject S' head (region of interest) along the image layer L. As shown in the drawing, the image layer L may be divided into more than two sections R1 and R2, wherein the imaging density of the second section is higher than that of the first section. As described above, the penetration data acquisition unit 320 may be configured to control the X-ray imaging unit 110 to perform radiography of a corresponding part of the region of interest based on the imaging density different from section to section of the imaging trajectory.

Referring again to FIG. 3, the penetration data acquisition unit 320 may be configured to control the driving of the rotating shaft 140 of the rotating member 120 of the X-ray imaging unit 110. Although in the above described embodiment, an example where the rotating shaft 140 moves linearly within the range of a predetermined length while rotating, namely, an example of two-axis driving is shown and explained, but the driving method of the rotating shaft 140 is not limited thereto. The driving method of the rotating shaft 140 may be an one-axis rotation that the rotating shaft 140 only rotates in a predetermined angle range, or may be a multi-axis driving that the rotating shaft 140 rotates and moves in a plane perpendicular to a longitudinal direction of the rotating shaft 140.

In an embodiment, the penetration data acquisition unit 320 may be configured to control the X-ray imaging unit 110 such that the rotating shaft 140 of the rotating member 120 moves linearly along an imaginary line passing through a center of an anterior tooth of the dental arch of the subject S at a constant velocity. However, the penetration data acquisition unit 320 may be configured to control the X-ray imaging unit 110 such that the rotating shaft 140 of the rotating member 120 moves linearly along the imaginary line passing through the center of the anterior tooth of the dental arch of the subject S at a velocity different from section to section of the dental arch.

The penetration data acquisition unit 320 controls of mechanical motion of the X-ray imaging unit 110, whereby a detection result detected by the X-ray sensor 124 of the X-ray imaging unit 110 is converted into the X-ray penetration data by the X-ray sensor 124 and selectively stored in a memory (not shown) of the X-ray imaging unit 110 itself. The acquired X-ray penetration data is managed in voxel units and addressing may be performed by the address of each voxel, that is, its three-dimensional location, as in the addressing. The acquired X-ray penetration data is moved to and stored in the storage 340 of the controller 150 under the control of the penetration data acquisition unit 320.

In the storage 340, data of parameters relating to radiography, such as the region of interest of the subject, the image layer in the region of interest, the imaging trajectory, the imaging density according to the imaging trajectory, may be stored, other than the X-ray penetration data. In addition, in the storage 340, various data required to operate X-ray image forming device 100 of the present invention, such as data relating to the control and operation of the X-ray imaging unit 110, may be stored.

The storage 340 may be in the form of one storage medium of flash memory type, hard disk type, multimedia card (MMC), card type memory (for example, SD (secure digital) card or XD (extreme Digital) card), RAM (random access memory), SRAM (static random access memory), ROM (read-only memory), EEPROM (electrically erasable programmable read-only memory), PROM (programmable read-only memory), magnetic memory, magnetic disk, and optical disk, but it will be understood that the storage 340 is not limited to the above forms by those skilled in the art.

The image reconstructor 330 may be configured such that the X-ray penetration data acquired by crossing through the image layer in the region of interest is selected to construct the projection data by location, and pixel data corresponding to the location is generated by backprojecting the constructed projection data by location to a corresponding location, namely, to each section of the image layer, thereby reconstructing the two-dimensional X-ray panoramic image of the image layer. Alternatively, the image reconstructor 330 may be configured such that the projection data by location is constructed for each location of the entire region of interest by selecting X-ray penetration data acquired by crossing through a corresponding location of the X-ray penetration data, and reconstructs the three-dimensional X-ray CT image of the entire region of interest. In this case, it is possible to acquire a two-dimensional X-ray panoramic image data by selecting a sectional image data of a location corresponding to a desired image layer from the reconstructed three-dimensional X-ray CT image. Herein, the term 'backprojection' collectively refers to a process of summing by backprojecting the penetration data acquired in various directions to respective directions, and generally, it is well known as a kind of hermeneutical technique for reconstructing three-dimensional X-ray CT images, so a detailed description thereof will be omitted.

Now, the configuration of the image reconstructor 330 will be described in detail, with reference to FIG. 5, which is a block diagram illustrating an embodiment of a detailed configuration of an image reconstructor shown in FIG. 3.

Figure 5:
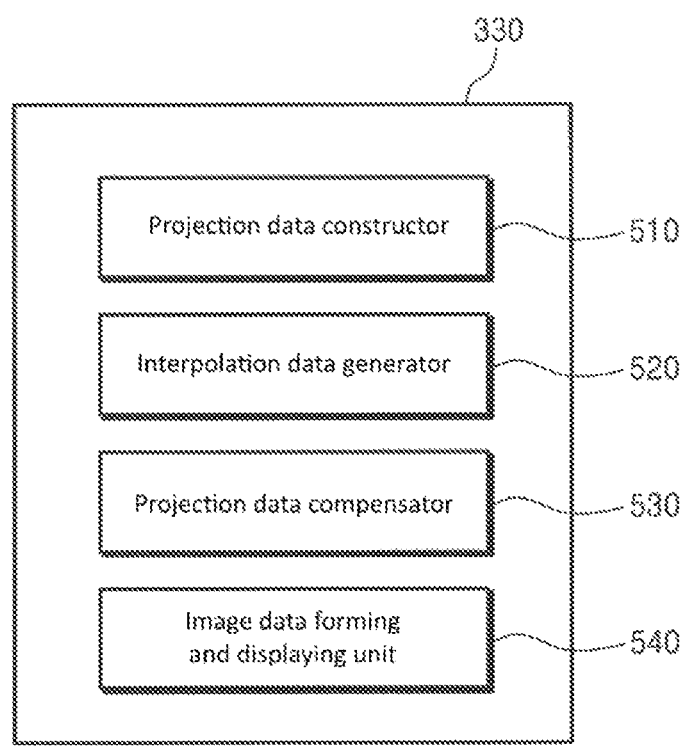
FIG. 5 is a block diagram illustrating an embodiment of a detailed configuration of an image reconstructor shown in FIG. 3.

Referring to FIG. 5, the image reconstructor 330 may include a projection data constructor 510. The projection data constructor 510 may be operated to construct projection data of a corresponding location, namely, projection data by location for each location of the region of interest or the image layer, by selecting X-ray penetration data acquired by crossing through the corresponding location, of the X-ray penetration data of stored in the storage 340. In this case, the projection data constructor 510 may be configured to select X-ray penetration data having a direction in a predetermined angle range at each location.

In an embodiment, the projection data constructor 510 may be configured to select X-ray penetration data acquired by the X-ray beam from the X-ray source 122 penetrating in a normal direction at each section of the image layer—herein, the normal direction is a direction toward outside from a corresponding location (if the subject is a human, outside a face). In an embodiment, the projection data constructor 510 may be configured to select X-ray penetration data acquired by the X-ray beam from the X-ray source 122 penetrating through a corresponding location while satisfying an angle condition selected based on the above described normal direction.

According to an embodiment, the selected angle condition may be within an angle range from 10 degrees to 180 degrees based on the normal direction. The angle range may be in the form of a solid angle, for example, a conical shape where the corresponding location is a vertex and an angle thereof is between 10 degrees and 180 degrees based on the above described normal direction. In an embodiment, the selected angle condition may be set as an angle range that gradually increases from the molar tooth of the dental arch to the anterior tooth.

As described above, at least one X-ray penetration data may be selected at each location of the image layer, and the selected X-ray penetration data at each location is referred to as 'projection data by location'.

The image reconstructor 330 may further include an interpolation data generator 520. The interpolation data generator 520 may be configured to generate interpolation data when penetration data in a specific angle direction is short in the projection data by location constructed in the projection data constructor 330. The interpolation data generator 520 may be configured to generate interpolation data for each location satisfying the angle condition selected based on the normal direction by an interpolation method using the corresponding projection data by location and/or the projection data by location of at least one adjacent location other than the corresponding location, for each location corresponding to the image layer.

The image reconstructor 330 may further include a projection data compensator 530. The projection data compensator 530 may be operated to compensate for each location corresponding to the image layer when the X-ray penetration data acquired by penetrating through a corresponding location at a specific angle satisfying an angle condition selected based on the normal direction is overlapped. In other words, the projection data compensator 530 may be configured to compensate for the projection data by location by adjusting a degree of overlap of the X-ray penetration data superimposed from the projection data by location.

The image reconstructor 330 may further include an image data forming and displaying unit 540. The image data forming and displaying unit 540 may be configured to form a two-dimensional X-ray panoramic image data of the image layer or a three-dimensional X-ray CT image data of the entire region of interest by using the projection data by location constructed in the projection data constructor 510 and compensated in the projection data compensator 530, and the interpolation data by location generated in the interpolation data generator 520. In particular, the image data forming and displaying unit 540 may be configured such that for each of locations corresponding to the image layer, the pixel data corresponding to the corresponding location is generated by backprojecting the projection data by location/the interpolation data by location at each section of the image layer, and this process is repeated for each location to form the two-dimensional X-ray panoramic image data of the image layer.

The image data forming and displaying unit 540 may be configured such that by using the image data formed described above, the three-dimensional X-ray CT image or the two-dimensional X-ray panoramic image of the image layer is shown to the user by rendering the same on a screen of the input/output unit 160. In an embodiment, image data forming and displaying unit 540 may be configured to display the three-dimensional X-ray CT image after displaying the two-dimensional X-ray panoramic image on a screen, but the reverse order is possible, and the two-dimensional X-ray panoramic image and the three-dimensional X-ray CT image are displayed simultaneously.

The above described embodiment may be realized by using at least one of application specific integrated circuits (ASICs), digital signal processors (DSPs), digital signal processing devices (DSPDs), programmable logic devices (PLDs), field-programmable gate arrays (FPGAs), processors, controllers, micro-controllers, and microprocessors in terms of hardware.

Embodiments including procedures, steps or functions, may be realized with firmware/software modules that are executable on a hardware platform that allows performing at least one function or operation. The software code may be realized by a software application written in a suitable program language. In this case, the software code may be stored in the controller 150 and executed. Although in the above described embodiment, it has been described that the X-ray imaging unit 110 is operated entirely under the control of the controller 150, some of the control functions of the controller 150, such as some or all of the functions of the penetration data acquisition unit 320, may be performed by the X-ray imaging unit 110.

According to the X-ray image forming device of the above described embodiment, the X-ray penetration data of the region of interest of the subject, including the dental arch, from the multiple directions is acquired through radiography at one time, and by using the X-ray penetration data, the three-dimensional X-ray CT image of the region of interest or the two-dimensional X-ray panoramic image of any image layer in the dental arch is formed through a simple calculation.

Figure 6:
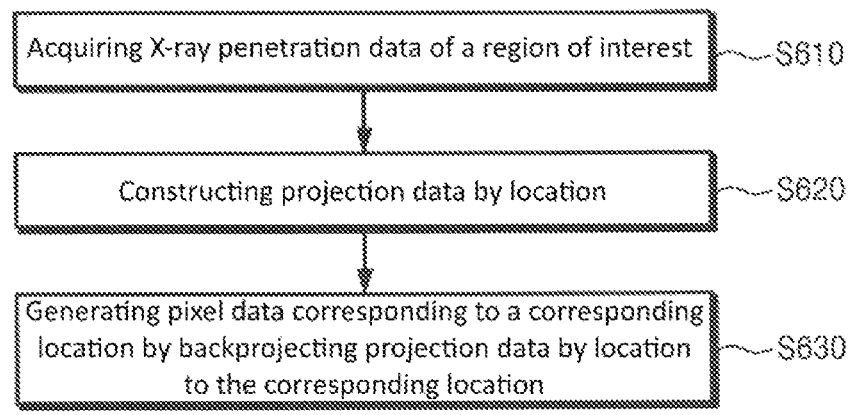
FIG. 6 is a flow chart illustrating an embodiment of an X-ray image forming method according to the present invention.

FIG. 6 is a flow chart illustrating an embodiment of an X-ray image forming method according to the present invention. Hereinbelow, reference will be mainly made to a case where the two-dimensional X-ray panoramic image of any image layer in the dental arch is obtained by using the X-ray penetration data from multiple directions of the region of interest.

An X-ray image forming method according to the present invention starts from step (S610) of acquiring the X-ray penetration data of the region of interest by emitting an X-ray beam to the region of interest of the subject and detecting the X-ray beam having penetrated through the region of interest. In step (S620), the projection data by location is constructed for each location corresponding to a predetermined image layer in the region of interest by selecting X-ray penetration data acquired by crossing through a corresponding location of the X-ray penetration data. The projection data by location may include the X-ray penetration data acquired by the X-ray beam from the X-ray source 122 penetrating through the corresponding location in the normal direction relative to the imaging trajectory. The reason why the projection data by location is configured to include the penetration data in the normal direction is to provide an image familiar to dentists by matching the cross-section direction of an X-ray panoramic image according to the present invention with the cross-section direction of a conventional X-ray panoramic image.

The projection data by location may further include the X-ray penetration data acquired by the X-ray beam from the X-ray source 122 penetrating through a corresponding location while satisfying an angle condition selected based on the above described normal direction. Herein, the selected angle condition may be within an angle range from 10 degrees to 180 degrees based on the normal direction. In an embodiment, the selected angle condition may be set as an angle range that gradually increases from the molar tooth of the dental arch to the anterior tooth. Thereby, it is possible to minimize intervention of data radiographed to the cervical vertebrae. In step (S630), for each of locations corresponding to the image layer, the pixel data corresponding to the corresponding location is generated by backprojecting the projection data by location constructed in step (S620) to the corresponding location, namely, at each section of the image layer.

Figure 7:
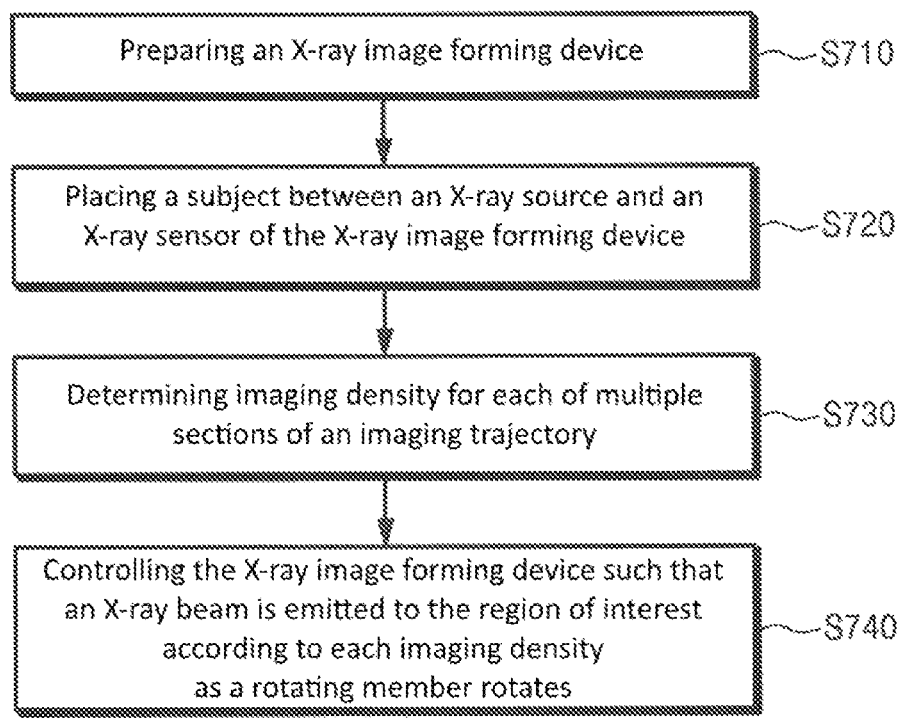
FIG. 7 is a detailed flow chart illustrating an embodiment of a step (S610) shown in FIG. 6.

FIG. 7 is a detailed flow chart illustrating an embodiment of a step (S610) shown in FIG. 6.

In step (S710), an X-ray image forming device is prepared. The X-ray image forming device may include an X-ray source 122 and an X-ray sensor 124 disposed to face each other, and a rotating member 140 rotatable about a rotating shaft and linearly movable. In step (S720), a subject is placed between the X-ray source 122 and the X-ray sensor 124 of the X-ray image forming device. In step (S730), the imaging trajectory set throughout the region of interest is divided into multiple sections, and the imaging density is determined, which corresponds to the number of irradiation times of X-ray beam from the X-ray source 122 to the region of interest corresponding to each section of the divided multiple sections. In step (S740), as the rotating member 120 rotates along the divided multiple sections of the imaging trajectory, the X-ray penetration data is acquired from the X-ray sensor 124 by controlling the X-ray image forming device such that the X-ray beam from the X-ray source 122 is emitted to the region of interest according to each imaging density. In step (S740), the X-ray image forming device may be controlled such that as the rotating member 120 rotates along the imaging trajectory at a constant velocity, the rotating shaft 140 moves linearly along the imaginary line passing through the center of the anterior tooth of the dental arch at a constant velocity.

Figure 8:
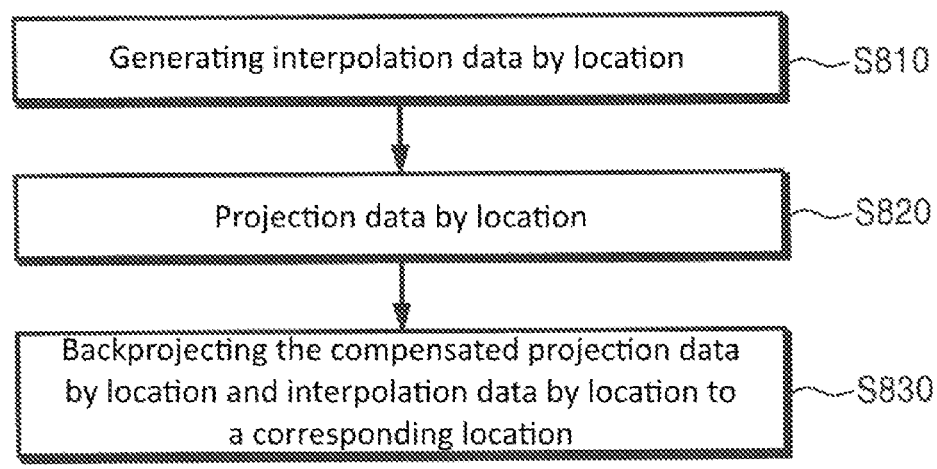
FIG. 8 is a detailed flow chart illustrating an embodiment of a step (S630) shown in FIG. 6.

FIG. 8 is a detailed flow chart illustrating an embodiment of a step (S630) shown in FIG. 6.

In step (S810), for each location corresponding to the image layer, the interpolation data for each location satisfying the angle condition selected based on the normal direction is generated by the interpolation method using the corresponding projection data by location and/or the projection data by location of at least one adjacent location other than the corresponding location. In step (S820), for each location corresponding to the image layer, the projection data by location is compensated by adjusting a degree of overlap of the X-ray penetration data superimposed from the projection data by location when the X-ray penetration data acquired by penetrating through a corresponding location at a specific angle satisfying an angle condition selected based on the normal direction is overlapped. In step (S830), the pixel data corresponding to the corresponding location is generated by backprojecting the projection data by location constructed in step (S620) and compensated in step (S820), along with the interpolation data by location generated in step (S810), to the corresponding location, namely, at each section of the image layer.

According to the above described embodiment of the present invention, a width of the X-ray sensor for radiography is not limited to a specific size. Accordingly, in order to realize the X-ray image forming method according to an embodiment of the present invention, the width of the X-ray sensor may be freely selected within a range between from 5 mm to 300 mm, or from a width of an X-ray sensor for a conventional panoramic scanning image forming device to a width of an X-ray sensor for a conventional cephalic CT. In other words, based on the premise of a dental X-ray image forming device, the width of the X-ray sensor that can be applied when a two-dimensional X-ray panoramic image is radiographed by using the X-ray image forming device according to embodiments of the present invention and may be larger than that of the X-ray sensor for the conventional panoramic scanning image forming device, and preferably, be freely determined below a width of a conventional CT sensor. For reference, assuming that a width of an X-ray sensor of a general panoramic scanning image forming device is between 5 mm and 10 mm, and a width of a CT sensor is a value of a magnification ratio*a width of region of interest (in the case of half beam scanning, ½(magnification ratio*region of interest의 width)), a width of the X-ray sensor of the X-ray image forming device according to embodiments of the present invention may be 6 mm or more and 100 mm or less, and preferably, is 20 mm or more and 70 mm or less.

Further, according to embodiments of the present invention, the imaging trajectory for moving the X-ray sensor is not particularly limited. Therefore, when the rotating member rotates and linearly moves to move the X-ray source and the X-ray sensor, it may rotate at a constant velocity and linearly move at a constant velocity, simultaneously.

Furthermore, according to embodiments of the present invention, the linear travel distance of the X-ray sensor is not particularly limited. Therefore, a reliable panoramic image can be formed even if radiography is performed at a shorter moving distance than a conventional panoramic scanning technique. In other words, based on the premise of a dental X-ray image forming device, the linear travel distance of the rotating shaft 140 of the X-ray image forming device according to embodiments of the present invention may be within a range from 0 mm to 60 mm, and preferably, is within a range from 20 mm to 50 mm when a two-dimensional X-ray panoramic image is radiographed.

Figure 9:
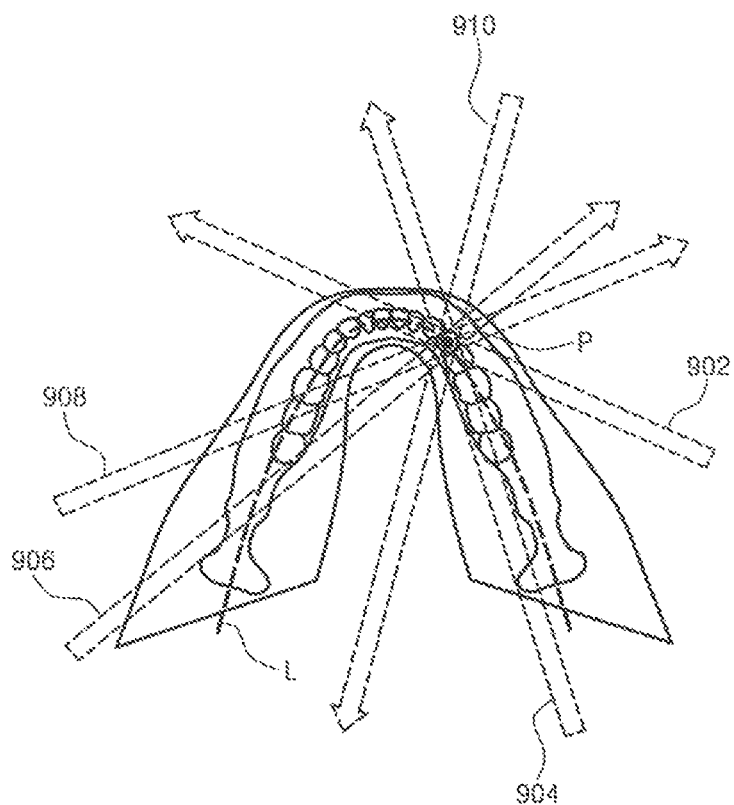
FIGS. 9 and 10 are views illustrating an embodiment of a performing process of the X-ray image forming method according to the present invention.
Figure 10:
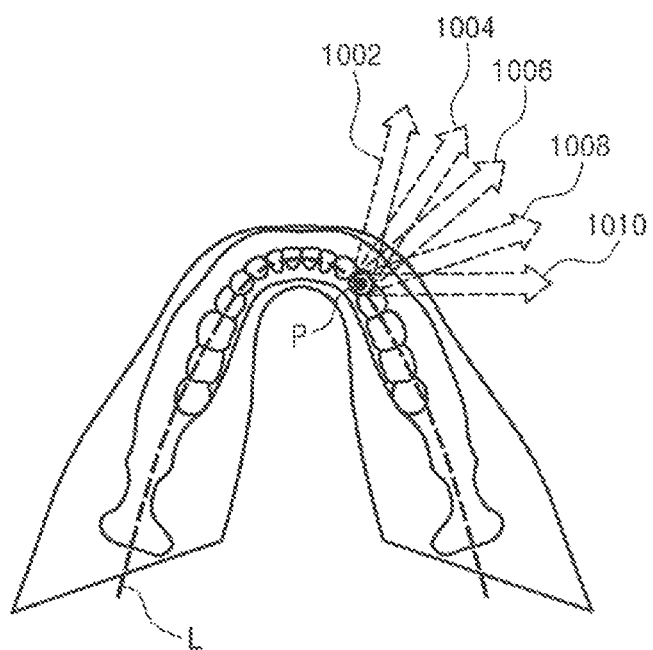

FIGS. 9 and 10 are views illustrating an embodiment of a performing process of the X-ray image forming method according to the present invention.

Referring to FIG. 9, X-ray beams 902, 904, 906, 908, and 910 from multiple directions crossing through a specific location P in the image layer L are shown. A direction of an arrow refers to a penetration direction of each X-ray beam. Referring to FIG. 10, of the X-ray beams from multiple directions crossing through the specific location P in the image layer L, projection data by location 1002, 1004, 1006, 1008, and 1010 selected within a predetermined angle range A at predetermined distances or at the predetermined number are illustrated. A direction of an arrow refers to a penetration direction of each X-ray beam.

In the projection data by location 1002, 1004, 1006, 1008, and 1010, as described above, the X-ray penetration data interpolated or compensated by interpolation or compensation process may be included. When A has a large value, a high-quality image may be obtained. On the other hand, when A has a small value, the data processing burden may be alleviated. If the distance between the selected X-ray penetration data within the same angle range is tight, the number of the X-ray penetration data included in the projection data by location 1002, 1004, 1006, 1008, and 1010 is large, whereby a high-quality image may be obtained; on the contrary, if the distance between the selected X-ray penetration data is wide, the number of the X-ray penetration data included in the projection data by location 1002, 1004, 1006, 1008, and 1010 is small, whereby the data processing burden may be alleviated.

Since recently, high-performance processor technology is rapidly evolving and the data processing capability of the X-ray image forming device may be enhanced, it is possible that the directions of each of the X-ray penetration data are held as closely as possible at equal distances by selecting the value of A as a large value. In case of constructing projection data by location with a relatively large angle range and a dense equal distance with the X-ray penetration data, since there are a lot of projection data for the corresponding location in the image layer, it is possible to sufficiently secure the number of backprojection, whereby the depth resolution of the X-ray panoramic image is improved and the image quality degradation factors such as the signal-to-noise ratio (SNR) may be reduced. Further, by making the thickness of the image layer thin, it is possible to obtain a clearer X-ray panoramic image.

Figure 11:
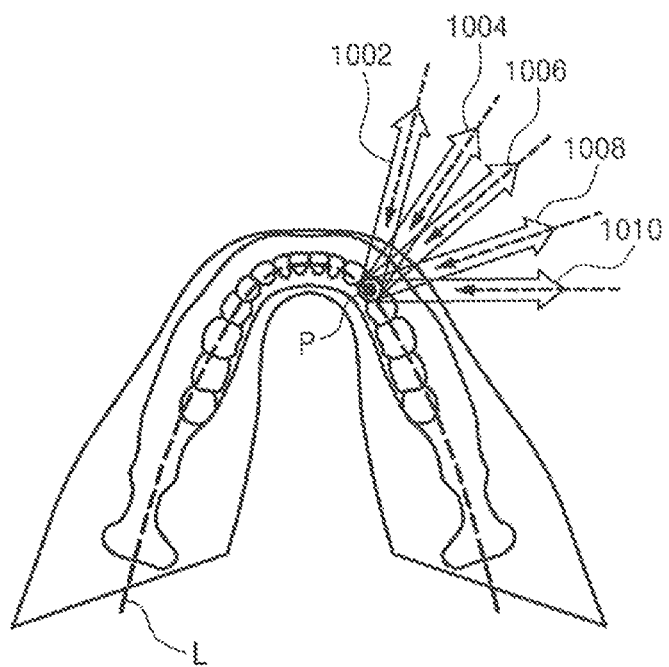
FIG. 11 is a conceptual view illustrating a process of backprojecting projection data by location.

Referring to FIG. 11, of the X-ray beams from multiple directions crossing through the specific location P in the image layer L, a process of backprojecting the projection data by location 1002, 1004, 1006, 1008, and 1010 selected within the predetermined angle range A at predetermined distances to each corresponding location P is conceptually shown.

Figure 12:
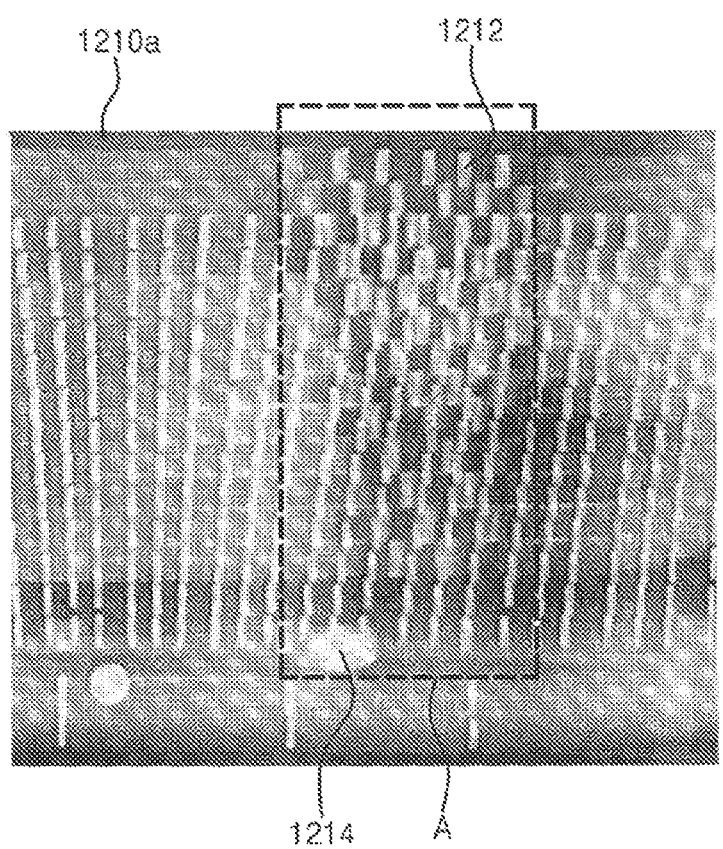
FIG. 12 is a photograph illustrating a result of forming an X-ray panoramic image according to a conventional panoramic scanning technique.
Figure 13:
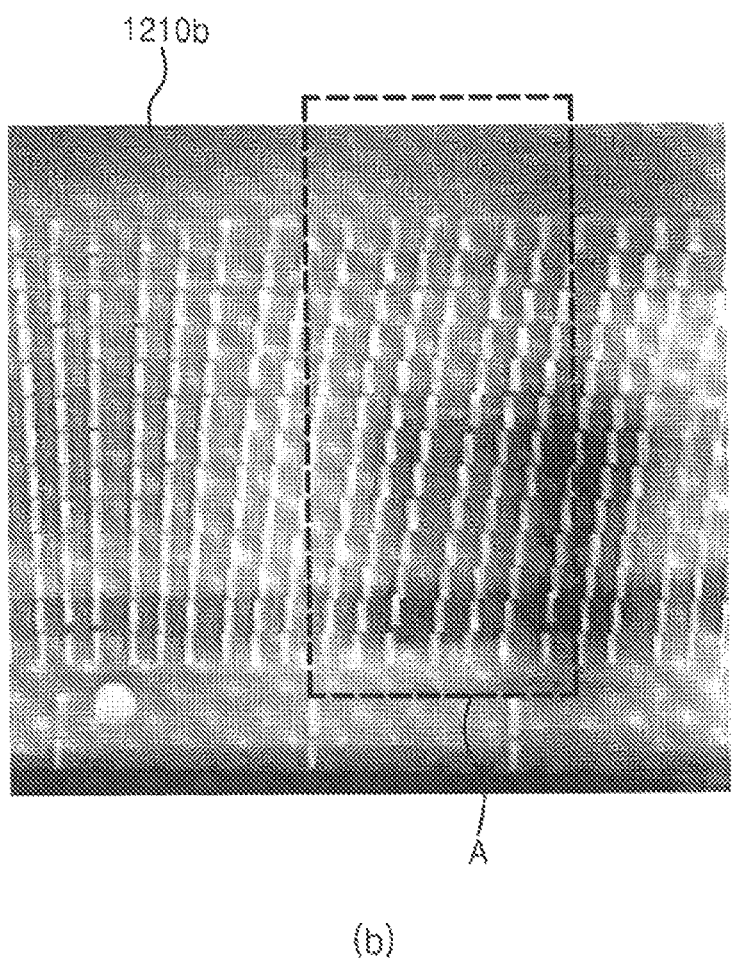
FIG. 13 is a photograph illustrating a result of forming an X-ray panoramic image according to an embodiment of an X-ray image forming method of the present invention.

FIGS. 12 and 13 are photographs respectively illustrating a result of forming an X-ray panoramic image according to a conventional panoramic scanning technique and a result of forming an X-ray panoramic image according to an embodiment of an X-ray image forming method of the present invention.

Referring to FIG. 12, in a part 1210a of an X-ray panoramic image formed by the conventional panoramic scanning technique, ghost effect 1212 and artifact 1214 occur in a marked area A. Referring to FIG. 13, a part 1210b of an X-ray panoramic image that is formed by an embodiment of the X-ray image forming device of the present invention and captured at the same position as illustrated in FIG. 12 is illustrated, wherein unlike in FIG. 12, a clear image without ghost effect or artifact in the marked area A is formed.

As described above, although reference to the embodiments has allowed the present invention to be described in more detail, it should be understood that the present invention is not limited to the embodiments but may be variously changed without departing from the technical idea of the present invention. Therefore, the embodiments disclosed in the present invention are not restrictive but are illustrative, and the scope of the technical idea of the present invention is not limited to the embodiments. The scope of the present invention should be interpreted by the accompanying claims, and it is to be understood that all technical ideas within the claims fall within the purview of the present invention.

The invention claimed is:

1. An X-ray image forming device comprising:
    an X-ray imaging unit including an X-ray source and an X-ray sensor to face each other with a region of interest therebetween, a moving member configured to rotate the X-ray source and the X-sensor about a rotating shaft and to move linearly;
    a penetration data acquisition unit configured to acquire X-ray penetration data from multiple directions crossing through an image layer in the region of interest by controlling the X-ray imaging unit, and further configured to control the X-ray imaging unit such that the X-ray penetration data includes penetration data penetrating through a substantial entire area of the region of interest by respectively penetrating through a part of the region of interest; and
    an image reconstructor configured to generate projection data within an angle range between 10 degree and 180 degree including a normal direction at each section of the image layer from the X-ray penetration data, for reconstructing a two-dimensional X-ray panoramic image of the image layer based on the projection data, and the image reconstructor further reconstructs a three-dimensional CT image of the entire region of interest based on the X-ray penetration data, and
    wherein the X-ray imaging unit moves continuously during the penetration data acquisition unit acquiring the X-ray penetration data from multiple directions.

2. The X-ray image forming device of claim 1, wherein the image reconstructor reconstructs the two-dimensional X-ray panoramic image by back projecting the projection data at each section of the image layer.

3. The X-ray image forming device of claim 1, wherein the region of interest includes a dental arch, the image layer is within the dental arch, and the predetermined angle range gradually increases from a molar tooth to an anterior tooth.

4. The X-ray image forming device of claim 1, wherein the image reconstructor includes an interpolation data generator configured to generate interpolation data in the predetermined angle range at each section of the image layer from the X-ray penetration data and generate the projection data based on both the X-ray penetration data and the interpolation data.

5. The X-ray image forming device of claim 1, further comprising:
    a projection data compensator configured to constantly compensate a number and a distance of the projection data at each section of the image layer.

6. The X-ray image forming device of claim 1, wherein the rotating shaft moves linearly at a constant velocity to acquire the X-ray penetration data.

7. The X-ray image forming device of claim 1, wherein the X-ray sensor has a width of 6 mm or more and 100 mm or less.

8. The X-ray image forming device of claim 7, wherein the X-ray sensor has a width of 20 mm or more and 70 mm or less.

9. The X-ray image forming device of claim 1, wherein the region of interest includes a dental arch, and the moving member moves linearly along a centerline passing through a center of an anterior tooth of the dental arch at a distance of 0 to 60 mm, to acquire the X-ray penetration data.

10. The X-ray image forming device of claim 9, wherein the moving member moves linearly along the centerline passing through the center of the anterior tooth of the dental arch at a distance of 20 mm to 50 mm, to acquire the X-ray penetration data.

11. The X-ray image forming device of claim 1, wherein the moving member includes at least one condition of three conditions: a first condition that the rotating shaft moves linearly at a constant velocity to acquire the X-ray penetration data; a second condition that the X-ray sensor has a width of 20 mm or more and 50 mm or less; and a third condition that the moving member moves linearly forwards and backwards along a centerline of the dental arch at a distance of 20 mm to 50 mm to acquire the X-ray penetration data.

12. The X-ray image forming device of claim 1, further comprising: a display configured to selectively or simultaneously display the two-dimensional panoramic image and the three-dimensional CT image on a screen.

* * * * *